(12) United States Patent
Tero

(10) Patent No.: US 10,076,625 B2
(45) Date of Patent: Sep. 18, 2018

(54) NASAL INTERFACE DEVICE

(76) Inventor: Robert Tero, Bayonne, NJ (US)

( * ) Notice: Subject to any disclaimer, the term of this patent is extended or adjusted under 35 U.S.C. 154(b) by 634 days.

(21) Appl. No.: 14/114,226

(22) PCT Filed: Apr. 29, 2012

(86) PCT No.: PCT/US2012/035713
§ 371 (c)(1),
(2), (4) Date: Oct. 28, 2013

(87) PCT Pub. No.: WO2012/149512
PCT Pub. Date: Nov. 1, 2012

(65) Prior Publication Data
US 2014/0066801 A1 Mar. 6, 2014

Related U.S. Application Data

(60) Provisional application No. 61/518,110, filed on Apr. 29, 2011.

(51) Int. Cl.
*A61M 15/08* (2006.01)
*A61M 16/06* (2006.01)
(Continued)

(52) U.S. Cl.
CPC ......... *A61M 16/0666* (2013.01); *A61B 5/097* (2013.01); *A61M 16/0057* (2013.01); *A61M 16/0858* (2014.02); *A61M 16/0875* (2013.01); *A61M 16/20* (2013.01); *A61M 16/209* (2014.02); *A61M 16/208* (2013.01); *A61M 2016/0027* (2013.01); *A61M 2205/584* (2013.01)

(58) Field of Classification Search
CPC .......... A61M 16/0866; A61M 16/0677; A61M 16/208; A62B 9/02; A62B 18/10
USPC ............ 128/207.18, 204.18, 204.26, 205.11, 128/205.24, 207.16
See application file for complete search history.

(56) References Cited

U.S. PATENT DOCUMENTS

| 1,125,542 A | 1/1915 | Humphries |
| 4,986,269 A | 1/1991 | Hakkinen |

(Continued)

FOREIGN PATENT DOCUMENTS

| EP | 1228781 | 8/2002 |
| WO | WO 2005/014080 | 2/2005 |

(Continued)

OTHER PUBLICATIONS

PCT Notification Concerning Transmittal of International Preliminary Report on Patentability for PCT application PCT/US2012/035713, dated Oct. 29, 2013.
(Continued)

*Primary Examiner* — Gregory Anderson
*Assistant Examiner* — Victoria Murphy
(74) *Attorney, Agent, or Firm* — Joseph E. Maenner; Maenner & Associates, LLC

(57) ABSTRACT

A nasal interface device delivers a high flow rate of a gas having a pressure that is adjustable to a patient. The device includes a nasal insert that is adapted to deliver pressurized breathing gas to a nasal cavity of the patient, and to receive expired air. The nasal insert has a pressurized breathing gas delivery port and an expired gas port. The expired gas port has a plurality of openings extending therethrough.

6 Claims, 15 Drawing Sheets

(51) Int. Cl.
  *A61B 5/097*   (2006.01)
  *A61M 16/08*   (2006.01)
  *A61M 16/20*   (2006.01)
  *A61M 16/00*   (2006.01)

(56) References Cited

U.S. PATENT DOCUMENTS

| | | | |
|---|---|---|---|
| 4,989,599 A | | 2/1991 | Carter |
| 5,018,519 A | * | 5/1991 | Brown ................ A61M 16/06 |
| | | | 128/203.29 |
| 5,046,491 A | * | 9/1991 | Derrick ................ A61B 5/097 |
| | | | 128/200.24 |
| 5,099,836 A | | 3/1992 | Rowland et al. |
| 5,360,000 A | * | 11/1994 | Carter ................ A61M 16/20 |
| | | | 128/204.26 |
| 5,682,881 A | | 11/1997 | Winthrop et al. |
| 6,017,315 A | | 1/2000 | Starr et al. |
| 6,478,026 B1 | | 11/2002 | Wood |
| 6,644,311 B1 | | 11/2003 | Truitt et al. |
| 6,851,425 B2 | | 2/2005 | Jaffre et al. |
| 6,874,500 B2 | | 4/2005 | Fukunaga et al. |
| 7,004,168 B2 | | 2/2006 | Mace et al. |
| 7,004,129 B2 | | 5/2006 | Truschel et al. |
| 7,168,429 B2 | | 1/2007 | Matthews et al. |
| 7,222,624 B2 | | 5/2007 | Rashad et al. |
| 7,225,809 B1 | | 6/2007 | Bowen et al. |
| 7,481,219 B2 | * | 1/2009 | Lewis .................... A61D 7/04 |
| | | | 128/206.11 |
| 7,574,368 B2 | | 8/2009 | Pawlikowski et al. |
| 7,665,465 B2 | | 2/2010 | Radney |
| 7,827,988 B2 | | 11/2010 | Matthew et al. |
| 7,877,817 B1 | | 2/2011 | Ho |
| 7,886,740 B2 | | 2/2011 | Thomas et al. |
| 7,931,026 B2 | | 4/2011 | Ho et al. |
| 7,938,114 B2 | | 5/2011 | Matthews et al. |
| 7,942,824 B1 | | 5/2011 | Kayyali et al. |
| 8,001,966 B1 | | 8/2011 | Goldstein et al. |
| 8,333,200 B2 | * | 12/2012 | Tero ................... A61M 16/0666 |
| | | | 128/204.18 |
| 2003/0140925 A1 | | 7/2003 | Sapienza et al. |
| 2004/0244804 A1 | | 12/2004 | Olsen et al. |
| 2006/0266361 A1 | * | 11/2006 | Hernandez ............ A61M 16/06 |
| | | | 128/206.11 |
| 2008/0190436 A1 | | 8/2008 | Jaffe et al. |
| 2010/0113956 A1 | | 5/2010 | Curti et al. |

FOREIGN PATENT DOCUMENTS

| | | | |
|---|---|---|---|
| WO | WO 2006125252 A1 * | 11/2006 | ........ A61M 16/0816 |
| WO | WO 2010/023590 | 3/2010 | |
| WO | WO 2010/091157 | 8/2010 | |

OTHER PUBLICATIONS

International Preliminary Report on Patentability for PCT/US2010/023159, dated Aug. 9, 2011.
International Search Report and Written Opinion for PCT/US2012/035713, dated Oct. 24, 2012.
Extended European Search Report for EP10739106.2 (PCT/US2010/023159), dated Mar. 27, 2015. 9 pages.

* cited by examiner

NASAL INTERFACE DEVICE

CROSS-REFERENCE TO RELATED APPLICATION

This application is a 371 of PCT application Serial No. PCT/US2012/35713, filed on Apr. 29, 2012, which claims priority from U.S. Provisional Patent Application Ser. No. 61/518,110, filed on Apr. 29, 2011, both of which are incorporated herein by reference in their entireties.

FIELD OF THE INVENTION

The present invention relates to a nasal interface device that functions to deliver high flow and has the ability to deliver pressurized breathing gas to a patient.

BACKGROUND OF THE INVENTION

Current respiratory ventilation systems to treat mild to moderate respiratory failure in humans, commonly of hypoxemic origin, include nasal Continuous Positive Airway Pressure (nCPAP) and humidified high flow therapy. nCPAP is the most widely used system because it can be administered non-invasively and can effectively increase patients functional residual capacity (FRC), allowing for air sacs to open and resulting in improved oxygenation. Diseases that can be treated with such a system include mild to moderate infant respiratory distress syndrome, atelectasis, pneumonia, pulmonary edema, congestive heart failure and many others in patients ranging from premature babies to adults. The nCPAP system, however, presents many problems, including the labor intensiveness of applying the head gear to the patient, and the bulky and cumbersome head gear that can lead to stress, claustrophobia and discomfort to patients. Physical conditions such as nasal irritation, pressure sores and skin breakdown are also a common complication.

The humidified high flow therapy system has the advantage of improved comfort as well as reduced risk of skin breakdown because of the smaller size of the head gear (i.e., nasal cannula). However, the humidified high flow therapy presents problems with uncontrolled pressurized environment, the risk of pressure build-up in the patient's respiratory cavity, and the inability of this therapy to control and set a CPAP. As a result of the known problems, clinicians are reluctant to apply this system due to the unregulated airway pressure (i.e., CPAP).

There exists a need to provide a small, lightweight and non-intrusive headgear with the ability to regulate pressure in the patient's respiratory cavity.

SUMMARY OF THE INVENTION

Briefly, the present invention provides a nasal interface device comprising a nasal insert adapted to deliver pressurized breathing gas to a nasal cavity of the patient, and to receive expired air. The nasal insert has a breathing gas delivery port and an expired gas port in fluid communication with the breathing gas delivery port. The expired gas port has a plurality of openings extending therethrough.

Further, the present invention provides a nasal interface device comprising a breathing gas inlet tube, first and second nasal prongs in fluid communication with the breathing gas inlet tube, and first and second expiratory tubes in fluid communication with the first and second nasal prongs. The first and second expiratory tubes are coupled to each other at an expiratory tube discharge portion. The expiratory tube discharge portion has at least one opening formed therein. An expiratory gas regulating member is operatively disposed over the at least one opening such that the expiratory gas regulating member is operable between a first position in which the at least one opening is at least partially covered by the expiratory gas regulating member and a second position in which the at least one opening is uncovered.

Additionally, the present invention provides a nasal interface device comprising a breathing gas supply having a first breathing gas supply tube and a second breathing gas supply tube and a nasal prong assembly. The nasal prong assembly comprises a first nasal prong in fluid communication with the first breathing gas supply tube, a second nasal prong in fluid communication with the second breathing gas supply tube, and an expiratory gas opening located between the first nasal prong and the second nasal prong.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILED DESCRIPTION OF EMBODIMENTS OF THE INVENTION

Figure 1:
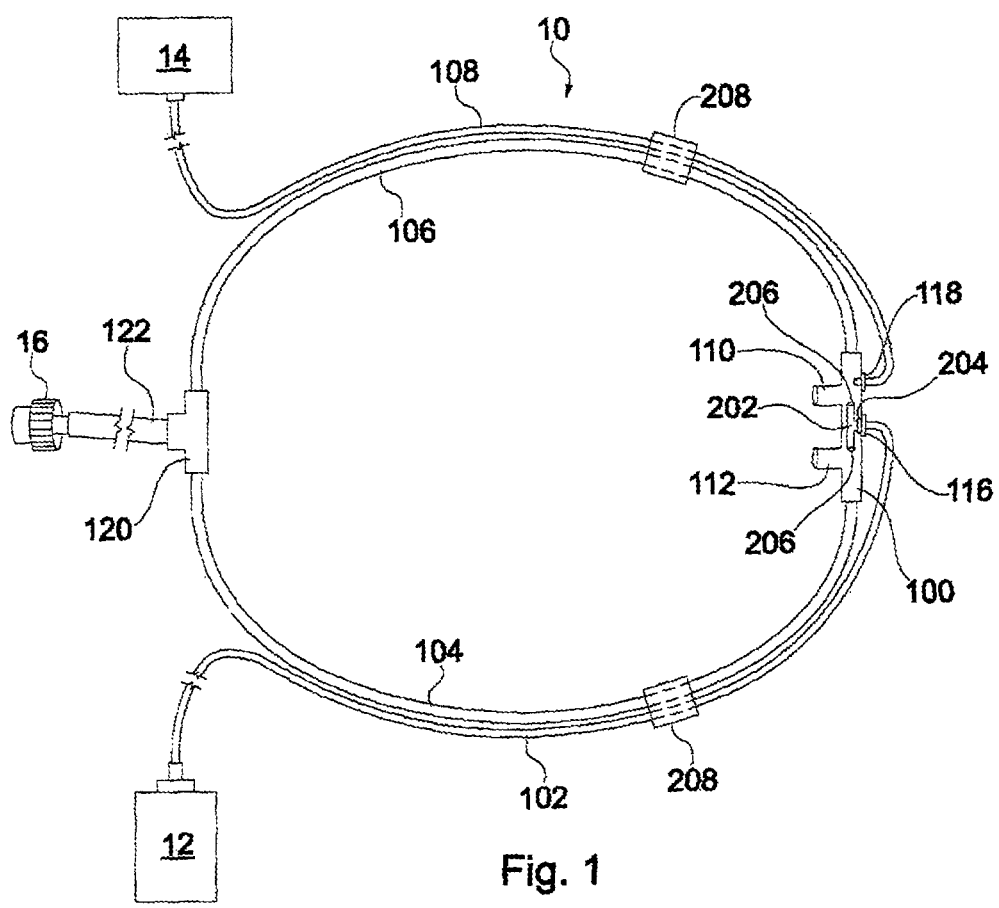
FIG. 1 depicts a respiratory ventilation system employing a nasal interface device, having a bidirectional tee flow deflector in the nasal insert, integrated with a breathing gas continuous positive airway pressure (CPAP) generator, a pressure measuring device and an expiratory limb pressure regulator in accordance with one embodiment of the present invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

Devices in accordance with the instant invention overcome the problems of the prior art. The user of the devices in accordance with the present invention is also provided with the ability to customize the inventive device according to the user's needs. Additionally, embodiments of the instant invention are adaptable such that they can be integrated with different respiratory ventilation systems. Furthermore, because the inventive devices may be customized to the size of the patient's facial features, the typical bulkiness and irritation of current respiratory ventilation systems that are capable of controlling CPAP are overcome. By applying one or more embodiments of the instant invention, patients can comfortably receive gas at a desired flow rate and clinicians can measure and easily adjust the CPAP.

Several advantages of the nasal interface device of the present invention include (a) its simplicity and small size, allowing the device to be easily applied with minimal treatment-patient interruption (i.e., it does not require the use of bulky headgear, nasal mask or head straps and thus reduces stress to the patient); (b) the ability to provide high flow and nCPAP; (c) the ability of the clinician to administer, regulate, and monitor nCPAP with little effort; (d) the adaptability and versatility of the device to be interfaced with most, if not all, respiratory ventilation systems and humidified high flow systems that are well-known to a skilled artisan; (e) the ability of the device to convert high flow systems, including but not limited to, Vapotherm and Fisher & Paykel systems, into a CPAP system; and (f) cost effectiveness because the device does not require many parts.

In accordance with one or more aspects of the present invention, a nasal interface device for delivering high flow and continuous positive airway pressure in a controlled and regulated manner to a patient is configured so that a clinician can quickly and easily apply the device to a patient, measure the CPAP and adjust the nCPAP accordingly. The nasal interface device is further configured so that a clinician can easily integrate the nasal interface device to existing respiratory ventilation systems and humidified high flow systems that are well-known to a skilled artisan.

In an exemplary embodiment, the nasal interface device comprises a nasal insert having a cavity in which a bidirectional tee flow deflector is situated, nasal prongs, and various tubing attachments. The nasal insert is configured to receive breathing gas, the gas generated from any generator well-known to a skilled artisan, through an injector tubing that enters the nasal insert through a bidirectional tee flow deflector. The breathing gas coming from the bidirectional tee flow deflector is directed towards and delivered in equal amounts through two nasal prongs into the nasal cavity of the patient. As the patient expires air through the nose into the nasal prongs, the expired air, along with any excess breathing gas, is directed by the bidirectional tee flow deflector through the nasal insert and into a series of expiratory tubes. This mixture of expired air and excess breathing gas travels through the expiratory tubes to the expiratory limb tubing and out to the environment through an expiratory limb pressure regulator. The flow of air and gas out of the expiratory limb pressure regulator can be adjusted so that the pressure in the nasal interface can be maintained.

Additionally the nasal insert may further be attached to pressure tubing connected to a pressure measuring device, such as a manometer, and expiratory limb tubing connected to an expiratory limb pressure regulator. The clinician can measure the gas pressure in the nasal insert by the manometer and adjust the expiratory limb pressure regulator accordingly to increase or decrease the CPAP.

The nasal interface device creates a pressurized environment, whereby breathing gas is forced through the injector tubing, the bidirectional tee flow deflector of the nasal insert and exits the nasal prongs and/or the expiratory limb pressure regulator. The pressurized environment allows the breathing gas flow and the pressure (i.e., CPAP) to be monitored and controlled. The pressure can be monitored by attaching a manometer to the optional pressure tubing coming from the nasal insert.

Application of the nasal interface device on a patient can be customized to suit the age and size of the patient. Generally, the nasal prongs are placed near or in a patient's nostrils such that the nasal insert is resting just outside of the patient's nose. The nasal prongs may be narrow to fit a premature baby or wide to fit an adult. The nasal prongs may be straight or curved depending on whether the prongs are to be placed just outside the nasal cavity (i.e., in premature babies and neonates), or further inside the nasal cavity (i.e., in infants, children and adults). Within each age group, the thickness of the nasal prongs may be also adapted to affect the high flow rate of the breathing gas flow and/or the air pressure. The injector tubing and expiratory tubes, and optionally the pressure tubing, may be placed around the patient's head to aid in securing the nasal insert in place. The expiratory tubes may be flexible so as to allow a variety of configurations about the head. Optionally the expiratory tubes may be rigid and contoured so that they may be placed over the ears of the patient.

Turning now to the details of the drawings, FIG. 1 is a view of a nasal interface device 10, embodying one or more aspects of the present invention, that is integrated with a respiratory ventilation system (not shown). The nasal interface device 10 delivers a high flow rate of a gas having a pressure that is adjustable and can be controlled for a particular patient and includes a nasal insert 100 having a hollowed cavity in which a bidirectional tee flow deflector 202 is situated. The nasal insert 100 is adapted to deliver pressurized gas to a nasal cavity of the patient, and to receive and direct expired air. The nasal insert 100 also includes nasal prongs 110 and 112 and four openings that are connected to a series of tubing including an injector tubing 102 via a pressurized gas delivery port 116, a pressure tubing 108 via an outlet port 118, and expiratory conduits or tubes 104 and 106. It is contemplated that the pressurized gas delivery port 116 and outlet port 118 may be located at any position in the nasal insert 100. The expiratory tubes 104 and 106 are in fluid communication with a tubing connector device 120, with the tubing connector device 120 in fluid communication with an expiratory limb tubing 122 that is further connected to an expiratory limb pressure regulator 16.

The bidirectional tee flow deflector 202 includes an inlet end 204 coupled to the pressurized gas delivery port 116 and outlet ends 206. The bidirectional tee flow deflector 202 is situated in the hollow cavity of the nasal insert 100 such that the inlet end 204 is connected to the end of the injector tubing 102 and the outlet ends 206 are situated near the nasal prongs 110 and 112 such that any breathing gas flowing out of the outlet ends 206 would preferentially flow into the nasal prongs 110 and 112 upon inspiration of a patient. It is contemplated that the outlet ends 206 are shaped so as to aid in directing breathing gas exiting the outlet ends 206 towards the nasal prongs 110 and 112. It is also contemplated that the bidirectional tee flow deflector 202 is situated in the nasal insert 100 and shaped so as to aid in diverting air coming in from the nasal prongs 110 and 112, upon expiration of air by a patient, to the expiratory tubes 104 and 106. The bidirectional tee flow deflector 202 functions to direct the breathing gas flow towards the nasal prongs 110 and 112 and to evenly distribute the breathing gas between the nasal prongs 110 and 112, resulting in even air flow to both nasal cavities of the patient during inspiration. The bidirectional tee flow deflector 202 further functions to divert expired air and excess breathing gas flow to the expiratory tubing 104 and 106 during expiration. The dual function of the bidirectional tee flow deflector 202 results in breathing gas flow support during inspiration and reduced expiratory resistance, while allowing positive distending pressures and ultimately reduction of work of breathing. The bidirectional tee flow deflector 202 may be made from soft flexible material selected from any suitable biocompatible flexible material such as latex, silicone, rubber, carbon fiber, or other synthetic fiber. The bidirectional tee flow deflector 202 may also be made from rigid material selected from any suitable rigid biocompatible material such as plastic, metal, wood or any material that maintains its shape, and is resistant to breaking or snapping.

It is contemplated that the injector tubing 102 is tethered to a length of one of the expiratory tubes 104 and 106 via at least one removable connector 208 so as to reduce the risk of loose tubing being accidentally pulled or crimped. The removable connector 208 may also slide along the length of the tubing such that the loop resulting from the combined tubing and nasal insert 100 is adjustable in size, allowing the nasal interface device 10 to be tightened or loosened around the patient's head, and functions to safely hold the nasal insert 100 in place. It is also contemplated that the injector tubing 102 may be inserted inside one of the expiratory tubes 104 and 106, which functions to reduce the risk of entanglement of multiple tubing. Additionally, the injector tubing 102 and one of the expiratory tubes 104 and 106 and/or the pressure tubing 108 and one of the expiratory tubes 104 and 106 may be fused such that they form a dual or multiple lumen tubing. Heat from expired gases flowing through expiratory tube 104 may be used to heat the breathing gas in injector tubing 102, reducing the occurrence of rainout within injector tubing 102.

Breathing gas produced by a breathing gas generator 12 that is connected to the injector tubing 102 is delivered to the nasal insert 100 through the injector tubing 102. One end of the injector tubing 102 is inserted through the nasal insert 100 via a pressurized gas delivery port 116 centrally located between the nasal prongs 110 and 112 and is connected to the bidirectional tee flow deflector 202. As the breathing gas exits the injector tubing 102, the breathing gas is directed through the bidirectional tee flow deflector 202 and towards the nasal prongs 110 and 112 and into the nasal cavity of the patient.

A clinician can measure the CPAP pressure of the nasal interface device 10 by a pressure measuring device 14, for example a manometer or other device that is well-known to a skilled artisan, that is connected to the nasal interface device 10 such as by the pressure tubing 108.

CPAP is influenced by two factors—leaks that occur through the nose and mouth of the patient, and the clinician's control of the breathing gas flow adjusted to slightly exceed patient demands. These factors can be controlled by the nasal interface device 10 as depicted in FIG. 1. Leakage of gas, and thus pressure, through the nose of the patient may be controlled by varying the size and fit of the nasal prongs 110 and 112 (see FIGS. 3-5 below). CPAP is mechanically maintained using an expiratory limb pressure regulator 16 that is connected to the nasal interface device 10 by the expiratory limb tubing 122. It is contemplated that the expiratory limb pressure regulator 16 may be a positive end expiratory pressure (PEEP) valve, a water seal column, or other pressure regulator that is well-known by a skilled artisan. This is accomplished when breathing gas flows are introduced through the injection tubing 102 and a mixture of excess breathing gas and expired air from the patient flow to the expiratory limb pressure regulator 16. The expiratory limb pressure regulator 16 maintains the desired CPAP pressure in the nasal interface device 10 by reducing or increasing gas flow out of the nasal interface device 10 and ensures that the gas flow delivered to the patient does not exceed the desired CPAP pressure setting. For example, if a clinician measures the CPAP pressure using the manometer and then desires to increase the CPAP pressure in a nasal interface device 10 having a PEEP valve, the clinician may adjust the PEEP valve by the turning the valve to reduce the air flow out of the nasal interface device 10.

Figure 2:
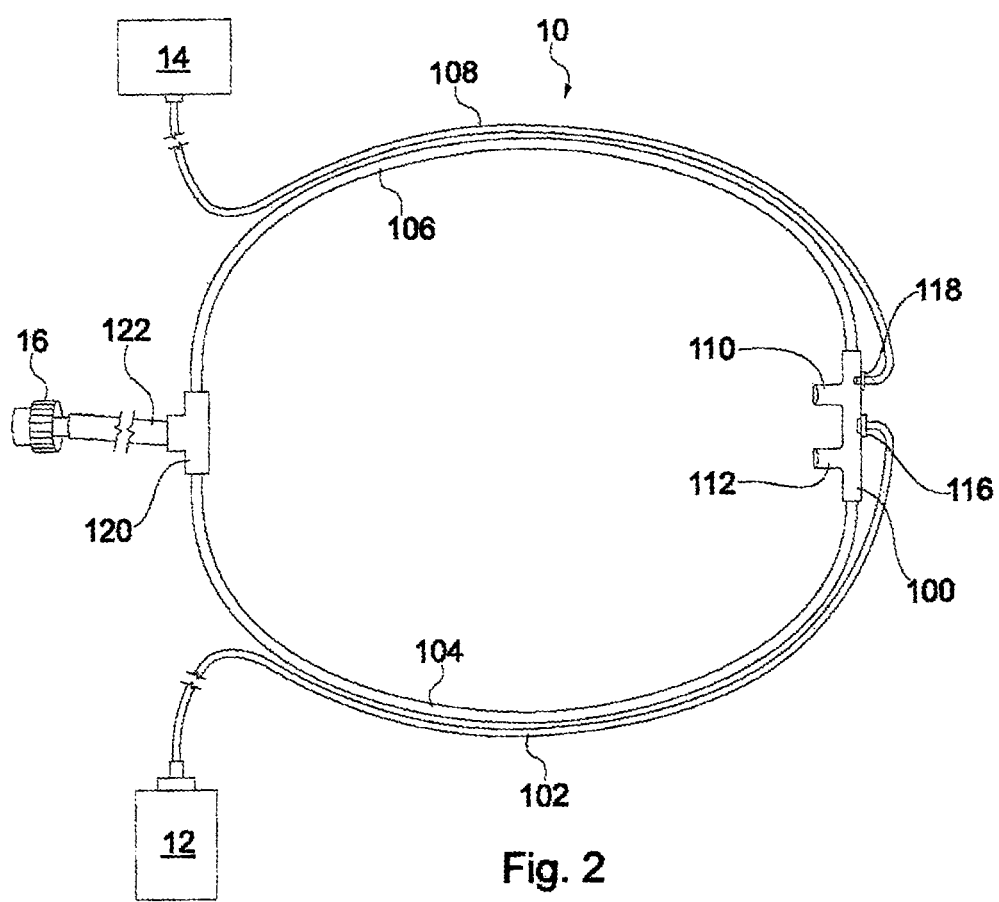
FIG. 2 depicts another embodiment of the nasal interface device of FIG. 1 without a bidirectional tee flow deflector in the nasal insert, and removable connectors to tether the injector tubing and expiratory tube or pressure tubing and expiratory tube together.

FIG. 2 is a view of the nasal interface device 10' in which the nasal insert 100' does not include the bidirectional tee flow deflector 202. One end of the injector tubing 102 is inserted through the nasal insert 100 via a pressurized gas delivery port 116 centrally located between the nasal prongs 110 and 112. As the breathing gas exits the injector tubing 102, the breathing gas flow is directed towards the nasal prongs 110 and 112 such that upon inspiration by the patient, the breathing gas is preferentially drawn through the nasal prongs 110 and 112 and into the nasal cavity of the patient.

Figure 3:
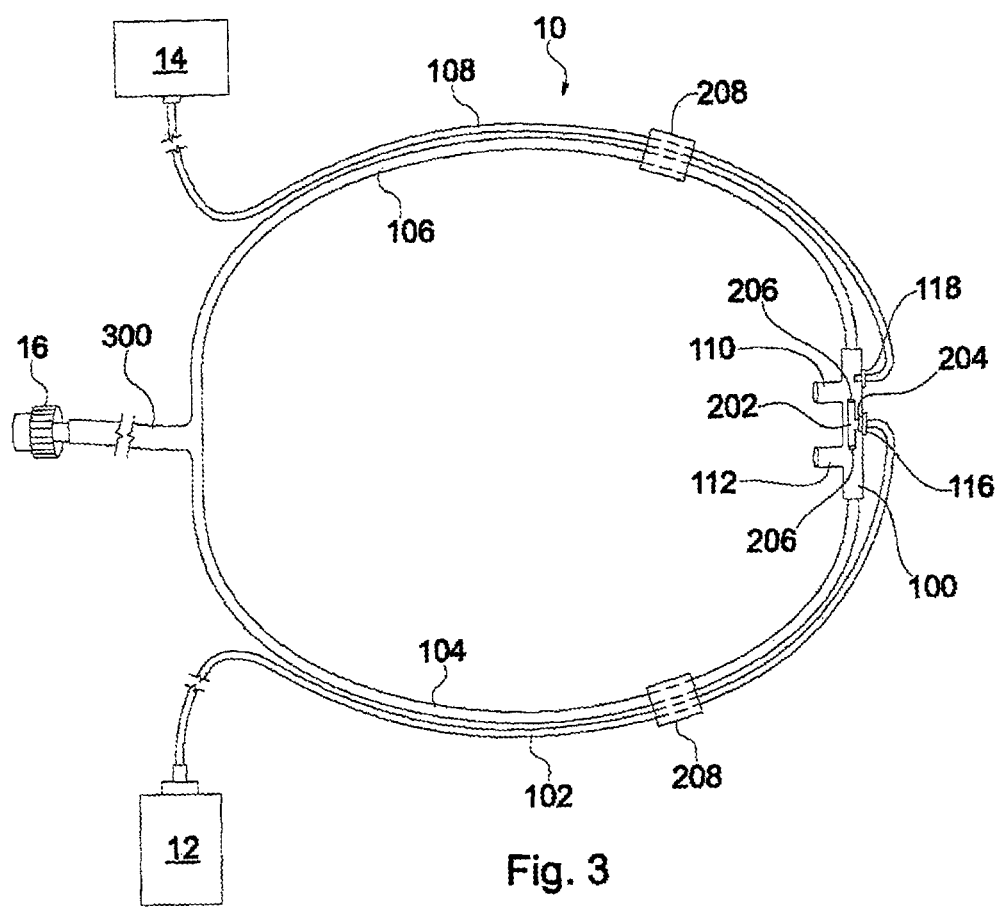
FIG. 3 depicts another embodiment of the nasal interface device of FIG. 1 in which the expiratory tubes are fused together and form a fused expiratory tube.

FIG. 3 is a view of the nasal interface device 10 in which the expiratory tubes 104 and 106 are joined together at a determined position along their lengths, without the use of the tube connector device 120, and form a fused expiratory tube 300. The fused expiratory tube 300 is further connected to an expiratory limb pressure regulator 16.

Figure 4:
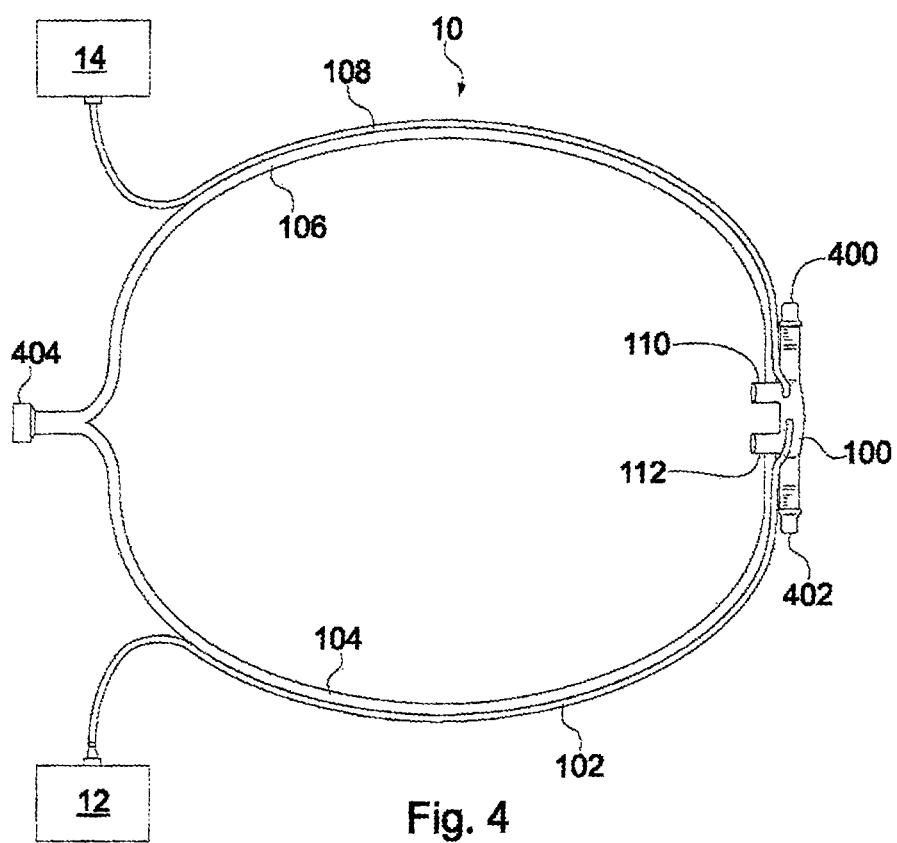
FIG. 4 depicts another embodiment of the nasal interface device of FIG. 3 having expiratory pressure regulators connected directly to the nasal insert.

FIG. 4 is a view of the nasal interface device 10 in which pressure regulators 400 and 402 are integral with the nasal insert 100. The pressure regulators 400 and 402 may be a PEEP valve, or other pressure regulator that is well-known by a skilled artisan. The pressure regulators are adjustable and controllable and function to regulate the air pressure (CPAP).

Although not shown, it is contemplated that the nasal insert 100 is fused to a single pressure regulator. The expiratory limb tubing 122 is connected to an end cap 404. The end cap 404 prevents any gas from escaping from the expiratory tubes 104 and 106 so that air pressure can be maintained. It is also contemplated that the expiratory tubes 104 and 106 may be solid tubing, such that the expiratory tubes 104 and 106 would not fill with air and would function to aid in keeping the nasal interface device 10 situated on the patient and not affect the air pressure.

Figure 5A:
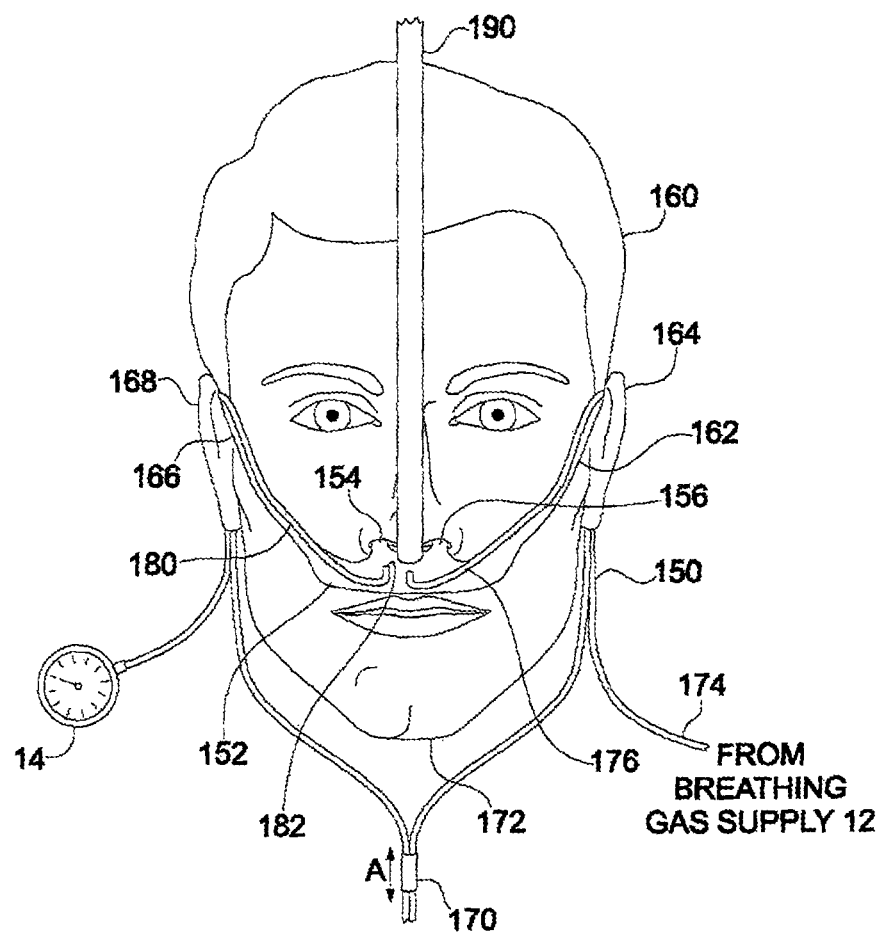
FIG. 5A depicts a front elevational view of another exemplary embodiment of a nasal interface device according to the present invention being used on a patient.
Figure 5B:
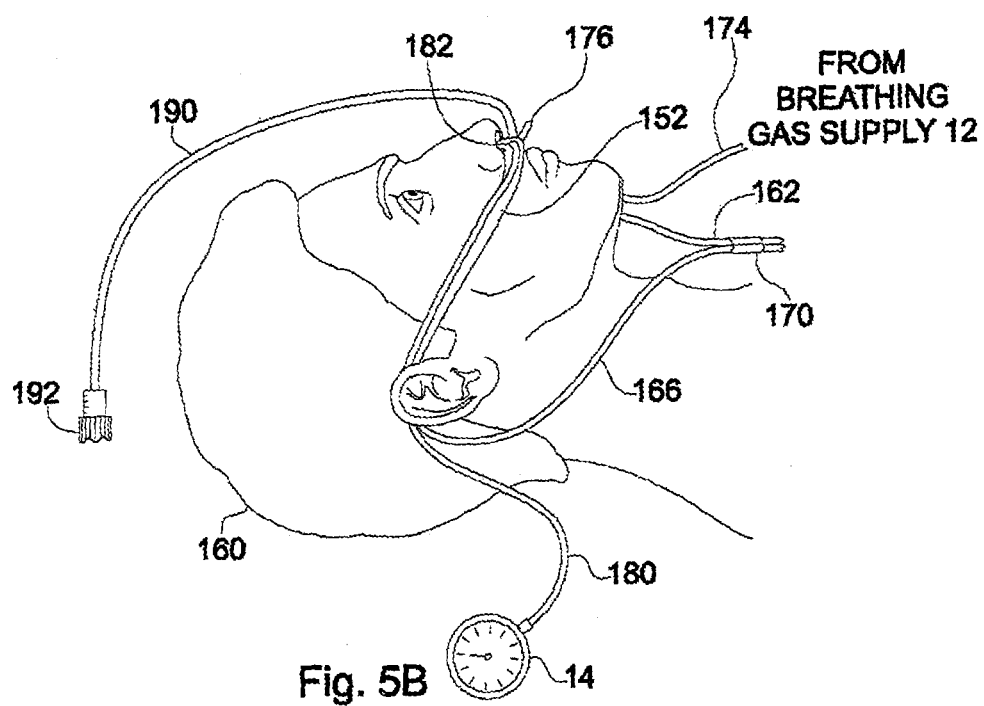
FIG. 5B depicts a side view of the nasal interface device of FIG. 5A being used in an exemplary fashion on the patient.

In an alternative exemplary embodiment of the present invention, illustrated in FIGS. 5A and 5B, a nasal interface device 150 includes a nasal insert 152 having nasal prongs 154, 156 that are insertable into the nares of a patient 160. Nasal insert 152 includes a first end portion 162 that extends from a side of nasal insert 152 and may be draped over the left ear 164 of the patient 160. First end portion 162 may then extend downward to the front of patient 160. Similarly, a second end portion 166 of nasal insert 152 extends from an opposing side of nasal insert 152 and may be draped over the right ear 168 of the patient 160. Second end portion 166 may then extend downward to the front of patient 160, where first and second end portions 162, 166 may be joined to each other by a slide collar 170. Slide collar 170 is adjustable along the length of first and second end portions 162, 166, as indicated by arrow "A", to secure nasal insert 152 under the patient's chin 172, as desired.

Nasal interface device 150 also includes a breathing gas supply conduit 174 that may be coupled to breathing gas supply 12 to provide breathing gas to nasal insert 152 and prongs 154, 156 for inhalation by the patient 160. Breathing gas supply conduit 174 extends along a length of first end portion 162 of the nasal insert 152, over the left ear 164 of the patient 160, and into nasal insert 152 at interface 176. Nasal insert 152 may include a tee flow deflector 202, illustrated in FIG. 1, or may omit the tee flow deflector, as illustrated in FIG. 2.

Pressure tubing 180 extends from nasal insert 152 via an outlet port 182. Pressure tubing 180 may extend along second end portion 166 of the nasal insert 152, over the patient's right ear 168, and to manometer 14, which measures the expiration pressure of the patient 160.

An exhaust conduit 190 extends from nasal insert 152 to exhaust expired air as well as non-inhaled breathing gas from inside nasal insert 152. A pressure regulator 192 is located at an end of exhaust conduit 190. Similar to pressure regulator 16 shown in FIGS. 1-3, pressure regulator 192 maintains the desired CPAP pressure in the nasal interface device 150 by reducing or increasing gas flow out of the nasal interface device 150 and ensures that the gas flow delivered to the patient does not exceed the desired CPAP pressure setting.

Figure 6:
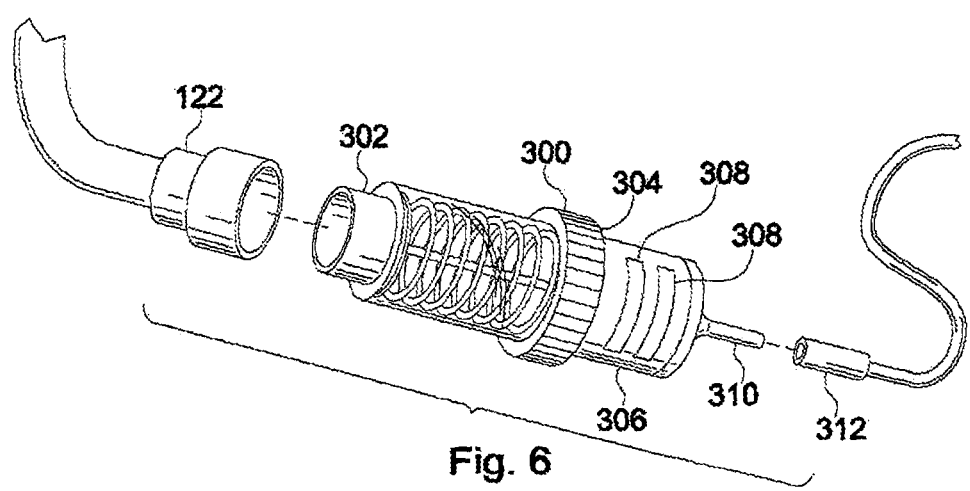
FIG. 6 depicts an exemplary embodiment of a positive end expiratory pressure valve (PEEP) pressure regulator for use with the nasal interface of the present invention.

A pressure regulator or PEEP valve according to an exemplary embodiment of the present invention is illustrated in FIG. 6. A known PEEP valve 300, such as, for example, a Threshold® PEEP valve, manufactured by Respironics of Murrysville, Pa., may be used. PEEP valve 300 includes an inlet 302 that is coupled to a discharge end of expiratory limb tubing 122 in place of expiratory limb pressure regulator 16 shown in FIGS. 1-3. An outlet 304 of PEEP valve 300 is coupled to a reservoir 306. Reservoir 306 includes at least one and, optionally, a plurality of, openings 308 therein to provide for fluid communication between the interior of reservoir 306 and atmosphere. A discharge end 310 of reservoir 306 is coupled to a suction tube 312. Suction tube 312 is coupled to a wall suction regulator/vacuum (not shown), which draws a vacuum on the interior of reservoir 306.

Openings 308 provide for airflow into reservoir 306 to allow minimal setting of vacuum yet still allow good amount of suction flow. If openings 308 are omitted, vacuum will affect the setting of PEEP valve 300 due to PEEP valve 300 becoming a closed system. Vacuum will thus pull vacuum directly from PEEP valve 300. Openings 308 further act as a safety mechanism in the event of inadvertent change in the vacuum or suction regulator and also allow for wide adjustment of the vacuum being drawn on PEEP valve 300. Further, a plurality of openings 308 act as a redundant feature in case of blockage of less than all openings 308.

PEEP valve 300 is used to remove excess moisture from the humidified expired gas that can collect in PEEP valve 300, which may possibly affect the function of PEEP valve 300 over time. With the vacuum on PEEP valve 300, PEEP valve 300 can be used with humidified breathing gas, which allows for long term use, as dry gas can cause discomfort to an adult patient and harm to an infant in long term applications. The use of PEEP valve 300 will allow clinicians to convert dry to a humidified application. For example, a dry application such as in an ambulance or labor and delivery can be initiated for a short term on the patient and when the patient is moved to the emergency department and/or neonatal intensive care unit, clinicians can convert to a humidified application with simply adding PEEP valve 300 for long term use without changing devices.

Figure 7:
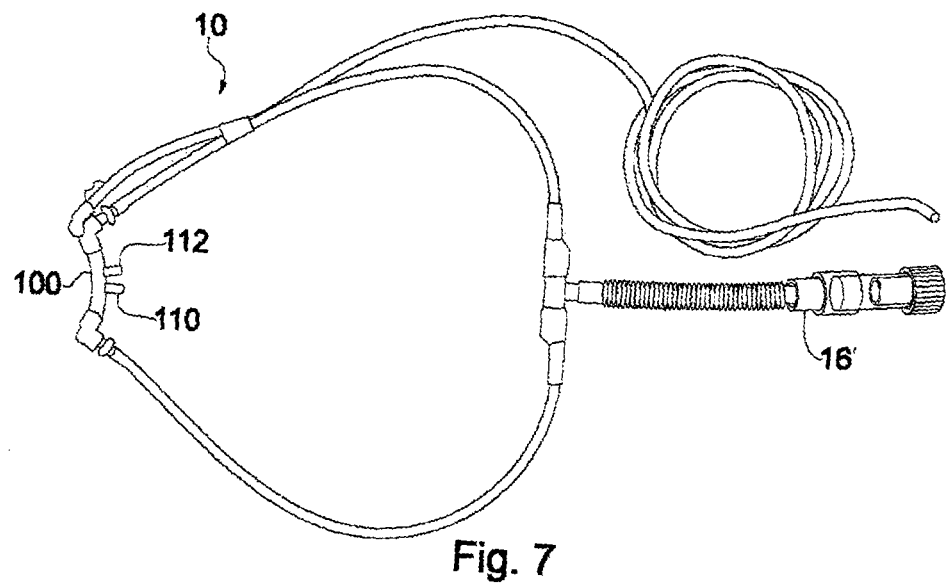
FIG. 7 depicts a nasal interface device having a nasal insert and nasal prongs suited for premature babies and neonates, and an expiratory limb tubing connected to a PEEP valve pressure regulator.
Figure 8:
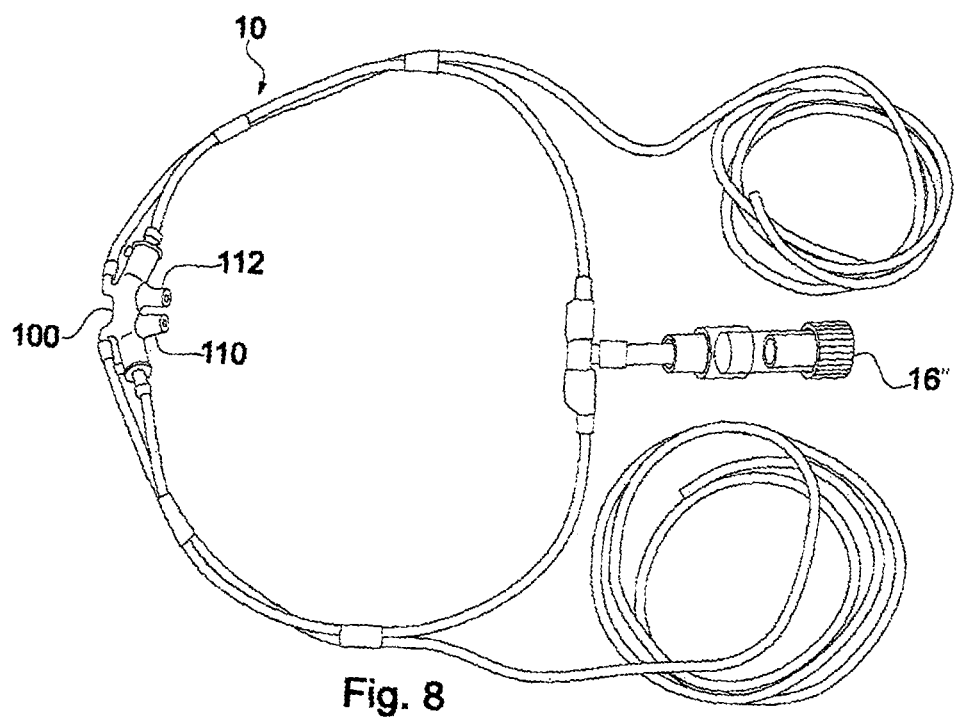
FIG. 8 depicts a nasal interface device having a nasal insert and nasal prongs suited for infants and adults, and an expiratory limb tubing connected to a PEEP valve pressure regulator.

FIGS. 7 and 8 show the nasal interface device 10 having variously sized nasal inserts 100 and expiratory limb pressure regulators 16. It is contemplated that the nasal insert 100 and nasal prongs 110 and 112 would vary in size and diameter depending upon the age and size of the patient, and also upon the desire to increase or decrease the high flow gas rate and air pressure. For example, FIG. 7 depicts the nasal interface device 10 showing the nasal insert 100 and nasal prongs 110 and 112 reduced in size suitable for premature babies and neonates, and a water seal column pressure regulator 16'. FIG. 8 depicts the nasal interface device 10 showing the nasal insert 100 and nasal prongs 110 and 112 customized to a size suitable for infants to adults, and a PEEP valve pressure regulator 16". It is also contemplated that the nasal prongs 110 and 112 may vary in shape such that they could take that shape of a straight shaft, curved, or anatomically shaped.

Nasal prongs 110 and 112 may be detachable from nasal insert 100. Nasal prongs 110 and 112 may be provided in a variety of shapes and/or sizes for selection based on the particular patient. For example, a child may require smaller nasal prongs than an adult in order to achieve the same level of sealing of the nasal prongs with the patient's nares. Alternatively, depending on the patient's physical condition, different sized nasal prongs may be required for different treatment regimens. For example, relatively loosely fitting nasal prongs may be desired to provide a deliberate leak between the nasal prongs and the patient's nares to improve $CO_2$ removal. Alternatively, a relatively tight seal between the nasal prongs and the patient's nares may be desired to obtain consistent air pressure for improved oxygenation to the patient.

Figure 9:
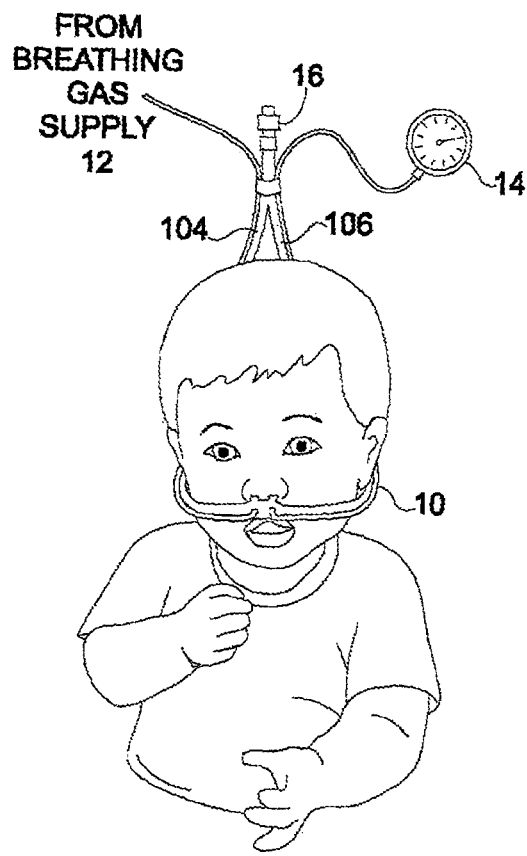
FIG. 9 depicts a nasal interface device having expiratory tubes being used by a neonate.
Figure 10:
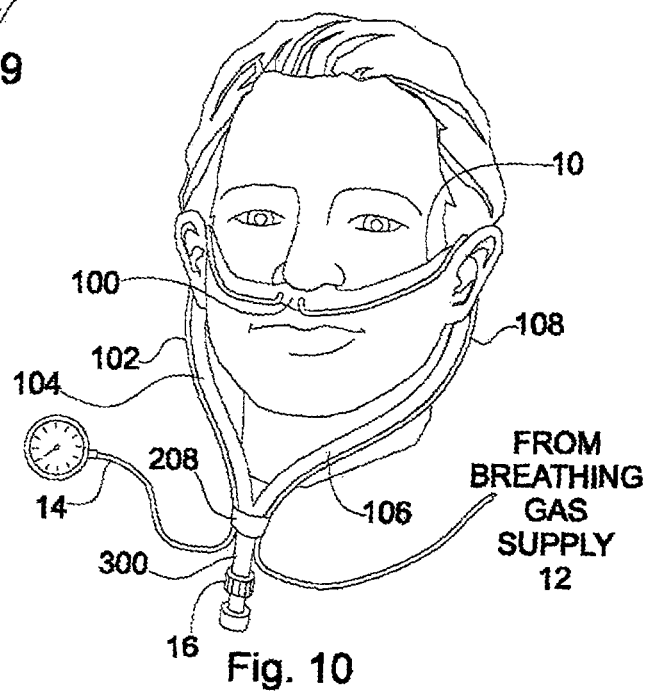
FIG. 10 depicts a nasal interface device having expiratory tubes contoured to fit over the ears being used by an adult.

FIGS. 9 and 10 depict the nasal interface device 10 being used by patients of varying age. It is contemplated that the expiratory tubes 104 and 106 may be flexible and/or corrugated so that the tubes may be contoured around a patient's head and shoulders. FIG. 9 shows a premature baby or neonate patient with a nasal interface device 10 having flexible expiratory tubes 104 and 106 that are easily contoured to wrap around the baby's head. It is also contemplated the expiratory tubes 104 and 106 may be rigid such that they are contoured a patient's head, for example, to wrap over the ears of a patient. FIG. 10 shows an adult patient with a nasal interface device 10 having rigid expiratory tubes 104 and 106 that are contoured to fit around the ears. The removable connector 208 is shown to tether the fused expiratory tube 300 and the injector tubing 102 and pressure tubing 108. The removable connector 208 may slide up or down, and as the removable connector 208 slides up (i.e., towards the patient's head) to a position that would tether together the expiratory tubes 104 and 106, injector tubing 102 and pressure tubing 108, a loop resulting by the combined tubing and nasal insert 100 will become reduced in size and functions to safely hold the nasal interface device 10 in place. To remove the nasal interface device 10 from the patient, the removable connector 208 can be easily slid down (i.e., away from the patient's head) along the tubing to increase the loop so that the nasal interface device 10 can be lifted away from around the patient's head.

Figure 11:
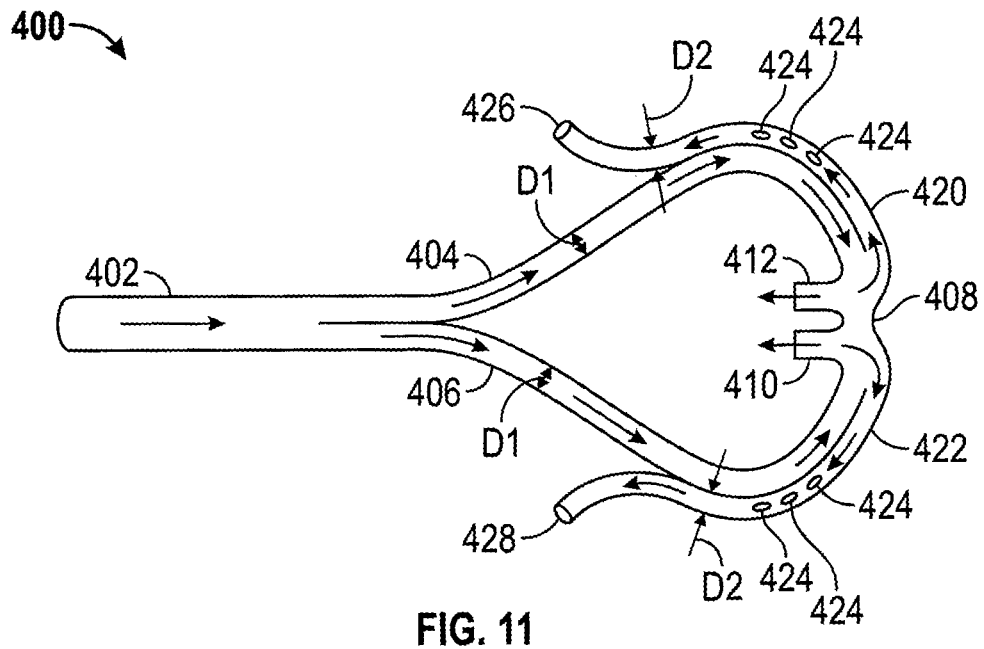
FIG. 11 illustrates a nasal interface device according to an alternative exemplary embodiment of the present invention, with a plurality of expiratory openings therein.

Additionally, both the length and inner diameter of the injector tubing 102, expiratory tubes 104 and 106 and pressure tubing 108 may vary to allow for different gas flow, pressures, and reduction of excess humidification (i.e., moisture build-up). Variations and relative differences in length and inner diameter will allow a clinician to set the desired pressure to be produced within the nasal interface device 10 and would allow for a range of flowrates, for example, low to very low flowrates. Referring now to FIG. 11, a nasal interface device 400 according to another exemplary embodiment of the present invention is shown. Nasal interface device 400 provides a humidified breathing gas inlet 402 that is connectable to a source of humidified breathing gas (not shown). Breathing gas inlet 402 divides into two supply tubes 404, 406 that each supply humidified breathing gas to either side of a nasal prong assembly 408. Supply tubes 404, 406 each have an internal diameter Dl. Nasal prong assembly 408 includes a pair of nasal prongs 410, 412 that are insertable into the nares of a patient (not shown) to discharge the humidified breathing gas into the nares. Nasal prongs 410, 412 can vary in size to accommodate use of nasal interface device 400 with CPAP.

Expiratory tubes 420, 422 are in fluid communication with nasal prong assembly 408 and allow expiratory gases from the nares to be discharged from nasal interface device 400. Expiratory tubes 420, 422 each have internal diameter D2, larger than internal diameter D1 in order to provide sufficient back pressure of expiratory gases within nasal interface device 400. Each expiratory tube 420, 422 includes a plurality of through holes 424 formed therein to allow expiratory gases to exit nasal interface device 400. Optionally, free ends 426, 428 of expiratory tubes 420, 422, respectively, may be open to further allow removal of expiratory gases. Alternatively, free ends 426, 428 may be closed, requiring all expiratory gases to exit through holes 424. As shown in FIG. 11, each expiratory tube 420, 422 includes three (3) through holes 424.

Figure 12:
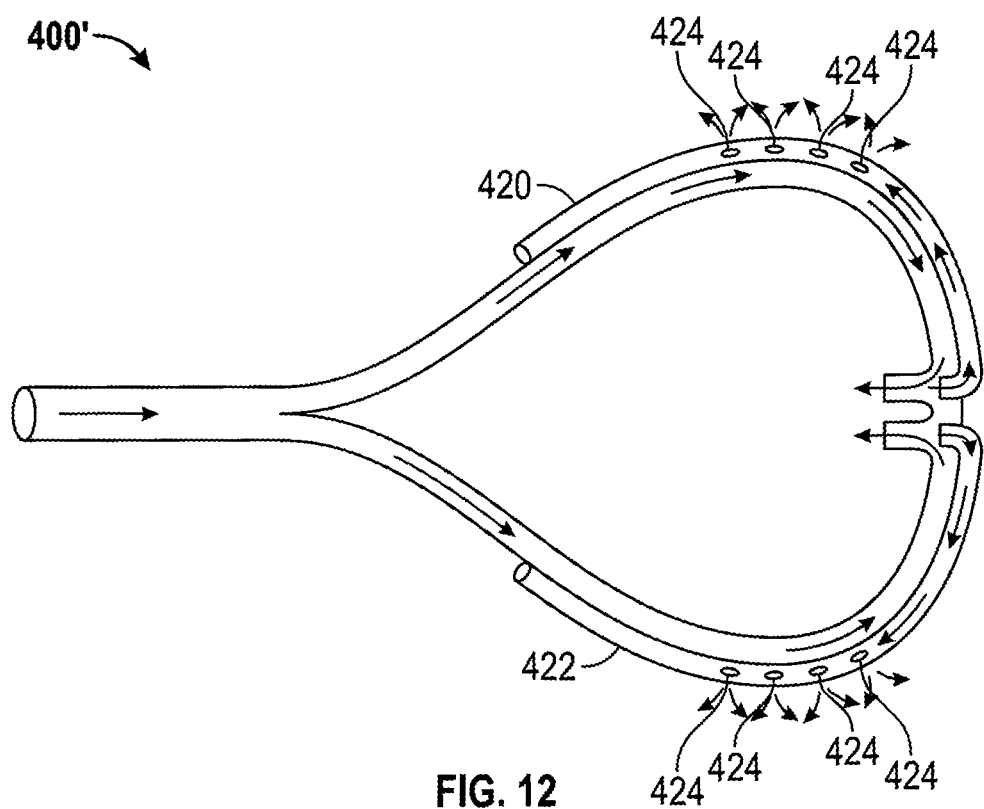
FIG. 12 illustrates the nasal interface device according to FIG. 11, with additional expiratory openings.

Based on the size of the patient on which nasal interface device 400 is being used, a different amount of through holes 424 may be required in order to successfully evacuate expiratory gases. For example, nasal interface device 400 having three through holes 424 in each expiratory tube 420, 422, as shown in FIG. 11, may be used for smaller patient, while a larger patient may require nasal interface device 400', shown in FIG. 12, which is the same as nasal interface device 400 shown in FIG. 11, with the exception of additional through holes 424 in expiratory tubes 420, 422. Instead of sizing nasal interface devices 400, 400' based on the size of the patient, nasal interface devices 400, 400' may tentatively be sized according to the respiratory needs of the patient.

Figure 12A:
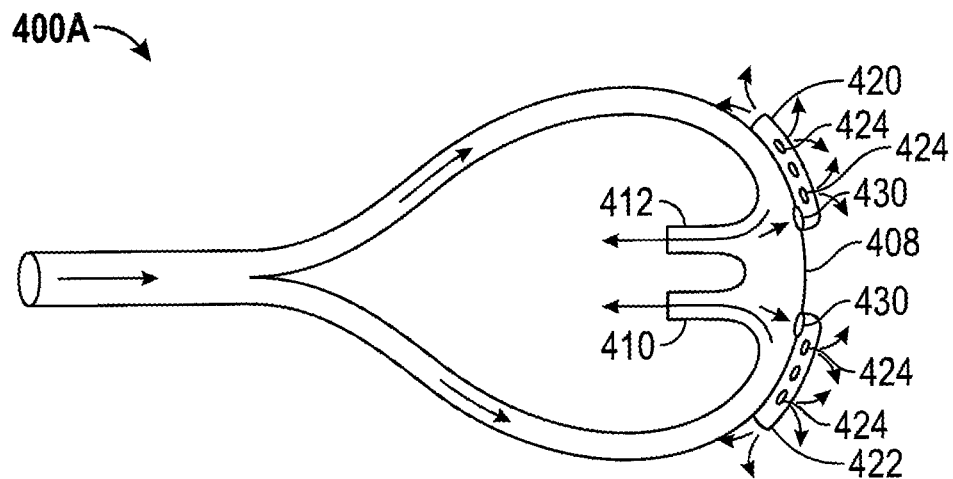
FIG. 12A illustrates a nasal interface device according to another alternative exemplary embodiment of the present invention, with short and expiratory tubes relative to the embodiments illustrated in FIGS. 11 and 12.

As shown in FIG. 12A, a nasal interface device 400A according to another exemplary embodiment of the present invention is disclosed. Nasal interface device 400A is similar to nasal interface devices 400, 400' with the exception that expiratory tubes 420, 422 end just distally of the last through holes 424. Additionally, nasal interface device 400A further includes a pair of expiratory openings 430 in nasal prong assembly 408, each expiratory opening 430 being generally collinear with each nasal prong 410, 412.

Figure 12B:
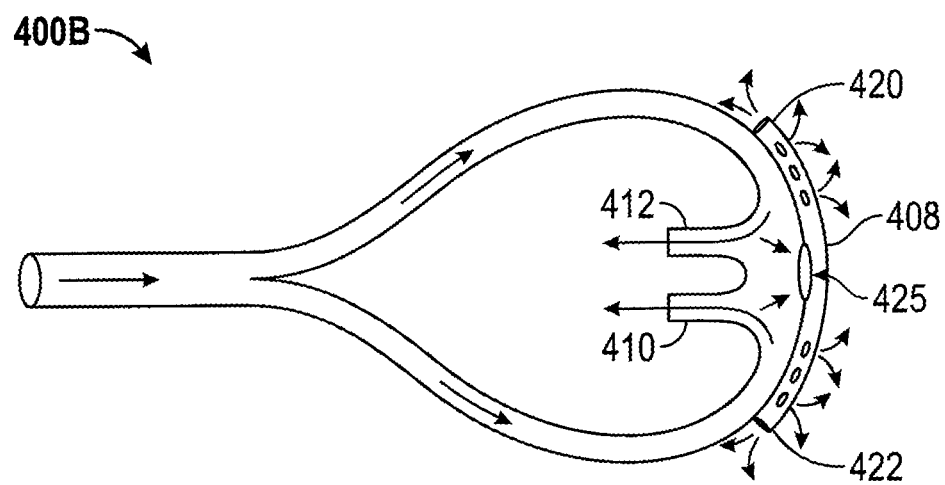
FIG. 12B illustrates a nasal interface device according to another alternative exemplary embodiment of the present invention, with a single large opening at the nasal prong assembly.

A nasal interface device 400B according to another exemplary embodiment of the present invention is disclosed in FIG. 12B. Nasal interface device 400B is similar to nasal interface device 400A with the exception of, instead of two expiratory openings 430 in nasal prong assembly 408, a single, larger expiratory openings 425 is located generally between nasal prongs 410, 412. Each of expiratory tubes 420, 422 may include an open and distal from large expiratory opening 425 to facilitate expiration of expiratory gases from nasal interface device 400B. Expiratory tubes 420, 422 may have a generally constant inner diameter.

Figure 12C:
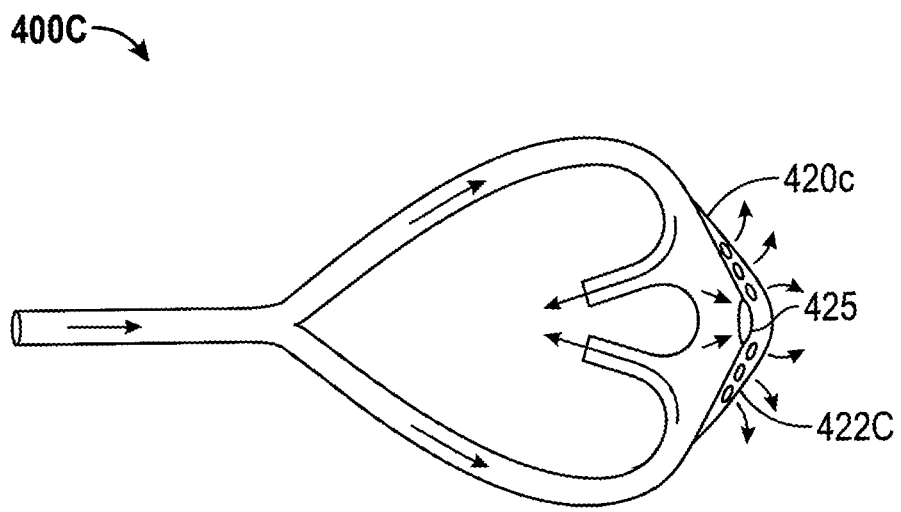
FIG. 12C illustrates a nasal interface device according to another alternative exemplary embodiment of the present invention, with tapered, closed expiratory tubes.

A nasal interface device 400C according to another exemplary embodiment of the present invention is disclosed in FIG. 12C. Nasal interface device 400C is similar to nasal interface device 400B with the exception of, instead of having expiratory tubes with an open end and a generally constant inner diameter, nasal interface device 400C includes expiratory tubes 420C, 422C have enclosed distal ends and a tapered inner diameter that tapers from a larger inner diameter proximate to expiratory opening 425 to a smaller inner diameter distal from expiratory opening 425.

Figure 12D:
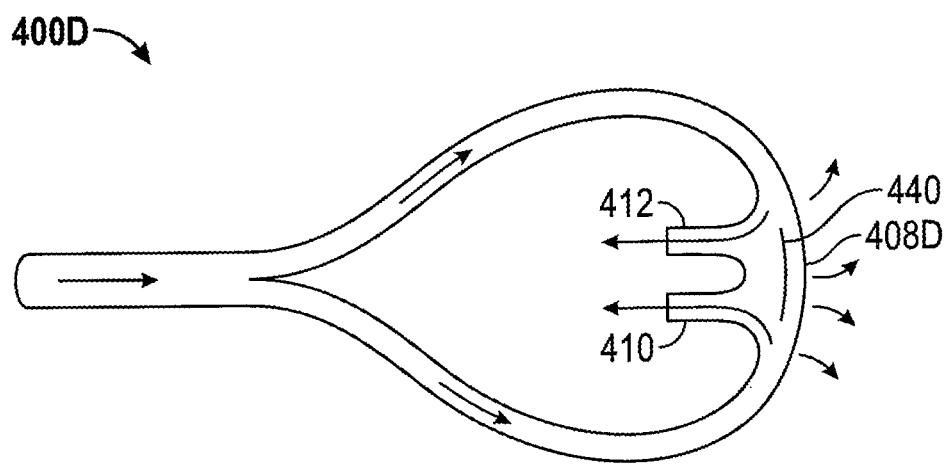
FIG. 12D illustrates the nasal interface device according to another alternative exemplary embodiment of the present invention, with an expiratory gas slit.

Nasal interface device 400D according to another exemplary embodiment of the present invention is disclosed in FIG. 12D. Nasal interface device 400D is similar to nasal interface device 400 with the exception that, instead of having expiratory tubes 420, 422 extending from nasal prong assembly 408, nasal interface device 400D includes a nasal prong assembly 408D that does not include any expiratory tubes, but instead includes a slit 440 that, in a natural, unbiased state, is closed, allowing breathing gas from a breathing gas source (not shown) to flow through nasal interface device 400D to nasal prong assembly 408D and two nasal prongs 410, 412 for inspiration by a patient (not shown). Upon expiration by the patient, increased pressure of expiratory gases in nasal prong assembly 408D forces slit 440 to open, allowing expiratory gases from the patient to escape nasal prong assembly 400D through slit 440. Note that, while a generally linear slit 440 is shown, slit 440 can be other shapes, including, for example, a cross, a checkerboard, scallops, or other shapes. Such alternative shapes may create an oscillatory effect that can potentially be beneficial for secretion movement and diffusion for gas exchange. It is believed by the inventor that such oscillatory effect may transmit vibrations or fluttering in the patient's airways or lungs. Clinical effects of oscillations are usually improved movement of secretions in the lungs as a result of agitated, or turbulent, gas flow through the airways. This turbulent flow may also enhance the presence of fresh gas in the lungs.

Figure 13:
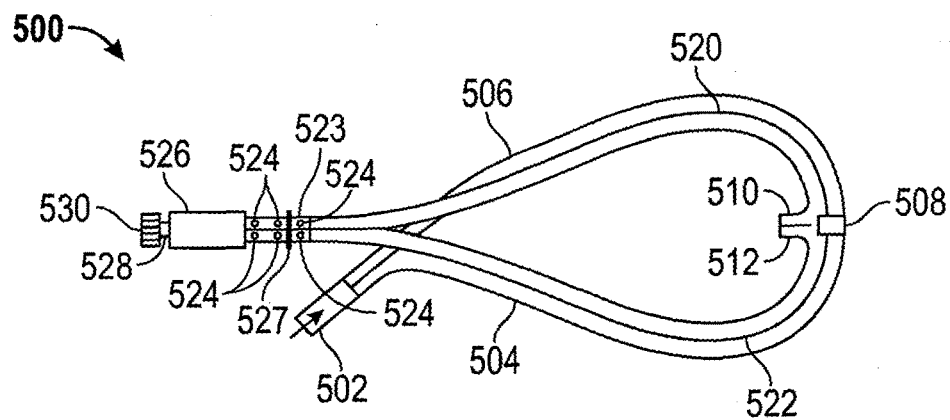
FIG. 13 illustrates a nasal interface device according to another alternative exemplary embodiment of the present invention.

Referring to FIG. 13, a nasal interface device 500 according to another exemplary embodiment of the present invention is disclosed. Nasal interface device 500 provides a humidified breathing gas inlet 502 that is connectable to a source of breathing gas (not shown). Breathing gas inlet 502 divides into two supply tubes 504, 506 that each supply humidified breathing gas to either side of a nasal prong assembly 508. While breathing gas inlet 502 is shown with two supply tubes 504, 506, those skilled in the art will recognize that breathing gas inlet 502 may be provided with only a single supply to having a first end in fluid communication with the source of breathing gas and a second end in fluid communication with nasal prong assembly 508. Nasal prong assembly 508 includes a pair of nasal prongs 510, 512 that are insertable into the nares of a patient (not shown) to discharge the humidified breathing gas into the nares.

Expiratory tubes 520, 522 are in fluid communication with nasal prong assembly 508 and allow expiratory gases from the nares to be discharged from nasal interface device 500. Expiratory tubes 520, 522 are connectable to each other at a discharge portion 523. Each expiratory tube 520, 522 includes a plurality of through holes 524 to allow expiratory gases to be discharged from nasal interface device 500. A sliding tube 526 is disposable over discharge portion 523 and is able to be slid along discharge portion 523 to occlude some or all of through holes 524, thereby adjusting the amount of expiratory gases that can be discharged from nasal interface device 500, resulting in the adjustment of the back pressure of expiratory gases and nasal prong assembly 508.

Optionally, a slide stopper 527 may be provided along the length of discharge portion 523 to prevent sliding tube 526 from occluding all through holes 524. As shown in FIG. 13, slide stopper 527 allows a single through hole 524 in each expiratory tube 520, 522 to remain open in the event that sliding tube 526 occludes the remaining through holes 524. Those skilled in the art, however, will recognize that slide stopper 527 may be located farther toward a discharge end 528 of discharge portion 523 in order that more than a single through hole 524 in each expiratory tube 520, 522 is permanently open.

Alternatively, discharge end 528 of discharge portion 523 may be equipped with a pressure relief valve 530 that allows expiratory gases to be discharged from expiratory tubes 520, 522 in the event that the back pressure within expiratory tubes 520, 522 exceeds a predetermined value.

Figure 14:
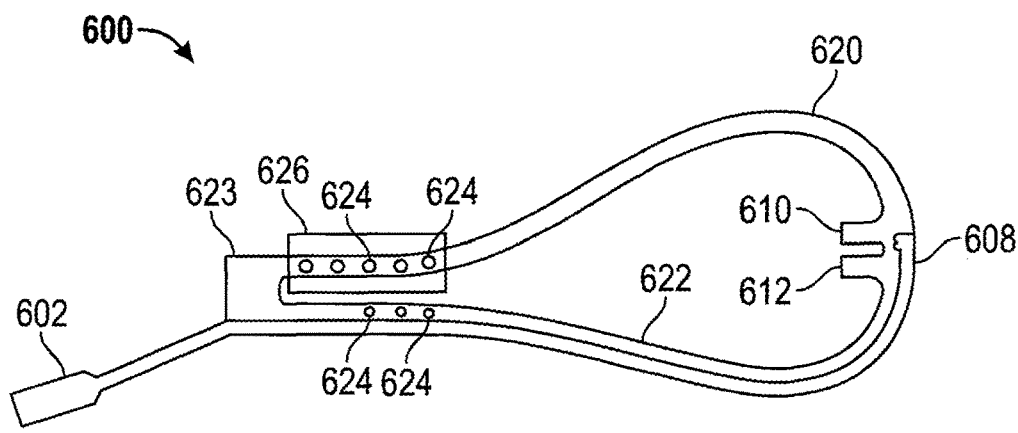
FIG. 14 illustrates a nasal interface device according to another alternative exemplary embodiment of the present invention, with a slide valve that is slidable over a plurality of expiratory openings.

Referring now to FIG. 14, a nasal interface device 600 according to an alternative exemplary embodiment of the present invention is disclosed. Nasal interface device 600 provides a humidified breathing gas inlet 602 that is connectable to a source of humidified breathing gas (not shown). Breathing gas inlet 602 provides breathing gas to a nasal prong assembly 608. Nasal prong assembly 608 includes a pair of nasal prongs 610, 612 that are insertable into the nares of a patient (not shown) to discharge the humidified breathing gas into the nares.

Expiratory tubes 620, 622 are in fluid communication with nasal prong assembly 608 and allow expiratory gases from the nares to be discharged from nasal interface device 600. In an exemplary embodiment, expiratory tubes 620 may have a larger inner diameter than expiratory tubes 622. As shown in all FIG. 14, expiratory tube 622 may be coupled to breathing gas inlet 602 along its length will expiratory tube 620 generally extends by itself from nasal prong assembly 608.

A discharge portion 623 of expiratory tubes 620, 622 may couple expiratory tubes 620, 622 to each other. Additionally, through holes 624 may be formed at discharge portion 623 in order to allow expiratory gases to be discharged from nasal interface device 600. A sliding tube 626 may be provided along expiratory tube 620 to allow through holes 624 in expiratory tube 620 to be occluded, as desired. Expiratory tube 622 may be free from a sliding tube so that through holes 624 in expiratory tube 622 cannot be occluded, thereby ensuring that expiratory gases can be discharged from nasal interface device 600. Sliding tube 626 may be slid along expiratory tube 620 in order to adjust the amount of expiratory gases being discharged from expiratory tube 620, thereby adjusting the back pressure at nasal prong assembly 608. Optionally, although not shown, a pressure relief valve may be inserted in discharge portion in order to prevent excessive back pressure in expiratory tubes 620, 622.

Figure 15:
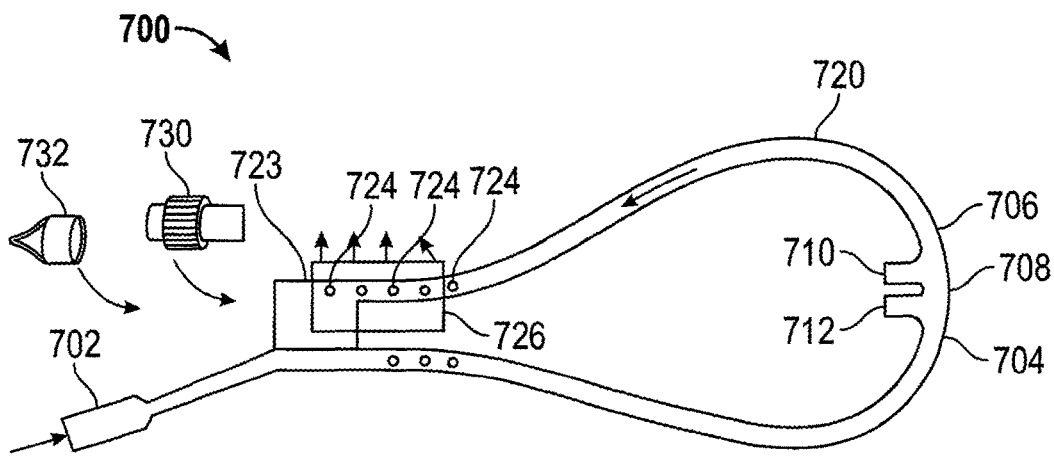
FIG. 15 illustrates a nasal interface device according to another alternative exemplary embodiment of the present invention, with optional pressure relief device.

A nasal interface device 700 according to an alternative exemplary embodiment of the present invention is shown in FIG. 15. Nasal interface device 700 provides a humidified breathing gas inlet 702 that is connectable to a source of humidified breathing gas (not shown). Breathing gas inlet 702 provides breathing gas to a first side 704 of a nasal prong assembly 708. Nasal prong assembly 708 includes a pair of nasal prongs 710, 712 that are insertable into the nares of a patient (not shown) to discharge the humidified breathing gas into the nares.

An expiratory tube 720 is in fluid communication with a second side 706 of nasal product assembly 708 to allow expiratory gases from the nares to be discharged from nasal interface device 700. A discharge portion 723 of expiratory tube 720 is coupled to breathing gas inlet 702. Expiratory tube 720 includes a plurality of through holes 724 at discharge portion 723 in order to allow expiratory gases to be discharged from nasal interface device 700. A sliding tube 726 may be provided along expiratory tube in order to allow through holes 724 in expiratory tube 720 to be occluded, as desired. Sliding tube 726 may be slid along expiratory tube 720 in order to adjust the amount of expiratory gases being discharged from expiratory tube 720, thereby adjusting the back pressure at nasal prong assembly 708. A PEEP valve 730 may be inserted in discharge portion 723 of expiratory tube in order to regulate pressure and to prevent excessive buildup of back pressure in the event that sliding tube 726 occludes all of through holes 724. Alternatively, instead of PEEP valve 730, a fluttering valve 732 may be inserted at the end of discharge portion 723 in order to ensure that expiratory gases can be expelled from expiratory tube 720.

Figure 16:
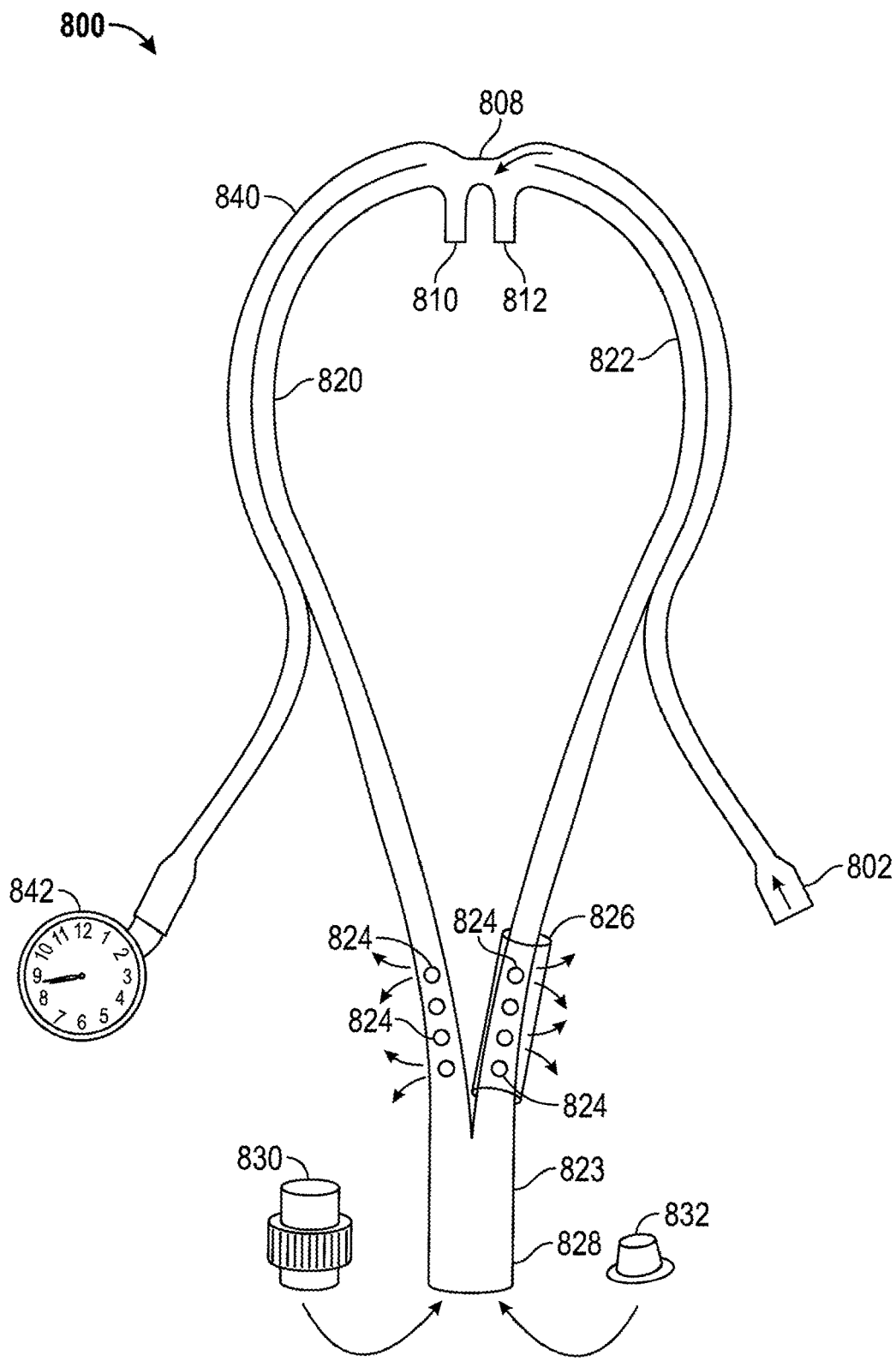
FIG. 16 illustrates a nasal interface device according to another alternative exemplary embodiment of the present invention; within optional pressure manometer.

Referring now to FIG. 16, a nasal interface device 800 according to an alternative exemplary embodiment of the present invention is shown. Nasal interface device 800 provides a humidified breathing gas inlet 802 that is connectable to a source of humidified breathing gas (not shown). Breathing gas inlet 802 provides breathing gas to a nasal prong assembly 808. Nasal prong assembly 808 includes a pair of nasal prongs 810, 812 that are insertable into the nares of a patient (not shown) to discharge the humidified breathing gas into the nares.

A pair of expiratory tubes 820, 822 are in fluid communication with nasal prong assembly 808 to allow expiratory gases from the nares to be discharged from nasal interface device 800. A discharge end of each of expiratory tubes 820, 822 is coupled together at a discharge portion 823. Each of expiratory tubes 820, 822 includes a plurality of through holes 824 proximate to discharge portion 823. A sliding tube 826 is slidingly disposed over discharge portion 823 and is slidable along expiratory tubes 820, 822 to occlude through holes 824 as desired. While all FIG. 16 shows sliding tube 826 apart from nasal interface device 800, those skilled in the art will recognize that sliding tube 826 is disposed over discharge portion 823 similar to sliding tube 526 shown in FIG. 13. A discharge end 828 of discharge portion 823 is open, allowing for the insertion of either a PEEP valve 830 or a plug 832 to be inserted therein.

A manometer tube 840 is coupled to nasal prong assembly 808. A manometer 842 is coupled to manometer tube 840 and is in fluid communication with nasal prong assembly 808. Manometer 842 is used to measure the back pressure in nasal interface device 800. Sliding tube 826 can be adjusted along the length of discharge portion 823 in order to adjust the back pressure at nasal prong assembly 808 as measured by manometer 842.

Figure 17:
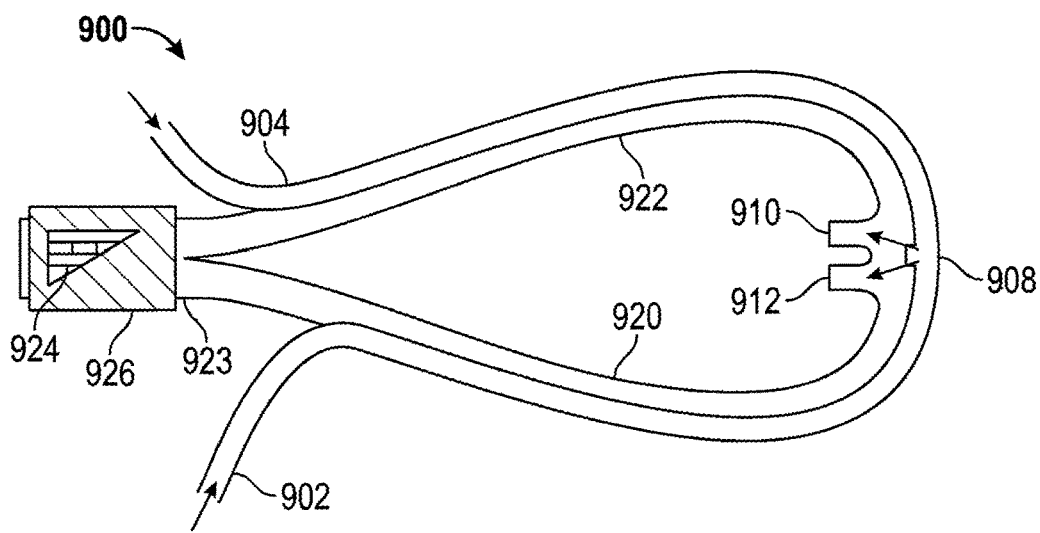
FIG. 17 illustrates a nasal interface device according to another exemplary embodiment of the present invention, with a titrating valve to regulate expiratory gases.

Referring now to FIG. 17, a nasal interface device 900 according to an alternative exemplary embodiment of the present invention is shown. Nasal interface device 900 provides a first humidified breathing gas inlet 902 and a second humidified breathing gas inlet 904 that are both connectable to a source of humidified breathing gas (not shown). First and second breathing gas inlets 902, 904 provide breathing gas to a nasal prong assembly 908. Nasal prong assembly 908 includes a pair of nasal prongs 910, 912 that are insertable into the nares of the patient (not shown) to discharge the humidified breathing gas into the nares.

A pair of expiratory tubes 920, 922 are in fluid communication with nasal prong assembly 908 to allow expiratory gases from the nares to be discharged from nasal interface device 900. A discharge end of each of expiratory tubes 920, 922 is coupled together at a discharge portion 923. Discharge portion 923 includes an elongated through opening 924 that allows expiratory gases to exit discharge portion 923. A titrating sleeve 926 is disposed around discharge portion 923 and is rotatable about discharge portion 923 to regulate the amount of through opening 924 that is occluded by titrating sleeve 926.

Figure 17A:
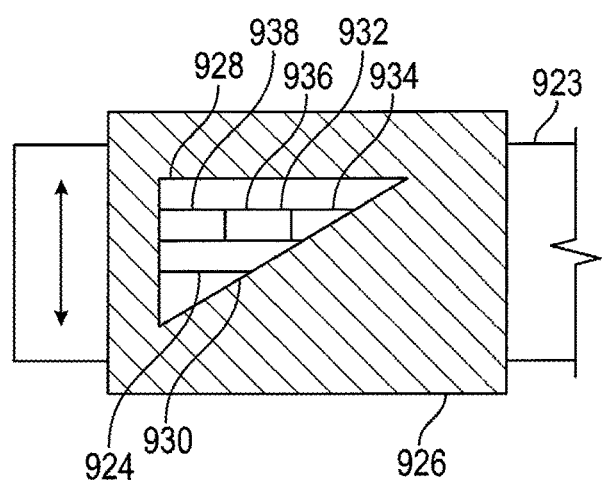
FIG. 17A illustrates an enlarged view of the titrating valve of FIG. 17.

An enlarged view of titrating sleeve 926 is shown in FIG. 17A. Discharge portion 923 can be color-coded to determine approximate back pressure based on the rotation position of titrating sleeve 926 relative to the through opening 924. By way of example only titrating sleeve 926 can include a right triangular opening 928 whose hypotenuse 930 extends across a color scale 932 along the length of through opening 924. Color scale 932 may include a green scale 934, a yellow scale 936, and a red scale 938 that, based upon the flow rate of humidified breathing gas being provided to nasal interface device 900, can provide proximate back pressures generated at nasal prong assembly 908. An exemplary chart, provided below, provides pressure values based on open and occluded prongs, simulating pressure relief when accidental occlusion of the patient's airway occurs. For example, for a flow rate of 5 liters per minute (LPM) of breathing gas provided to nasal interface device 900, with titrating sleeve 926 rotated such that hypotenuse 930 extends across green scale 934, open prong pressure is approximately 5 centimeters of water (cm $H_2O$) and occluded prong pressure is approximately 10 cm $H_2O$. If titrating sleeve 926 is rotated such that hypotenuse 930 extends across yellow scale 936 while maintaining the same flow rate, open prong pressure increases to approximately 7 cm $H_2O$ and occluded prong pressure increases to approximately 13 cm $H_2O$.

| Flow: | 3 LPM | 5 LPM | 7 LPM |
| --- | --- | --- | --- |
| Green | 3/8 | 5/10 | 8/12 |
| Yellow | 4/10 | 7/13 | 10/15 |
| Red | 5/12 | 9/15 | 13/18 |

Figure 18:
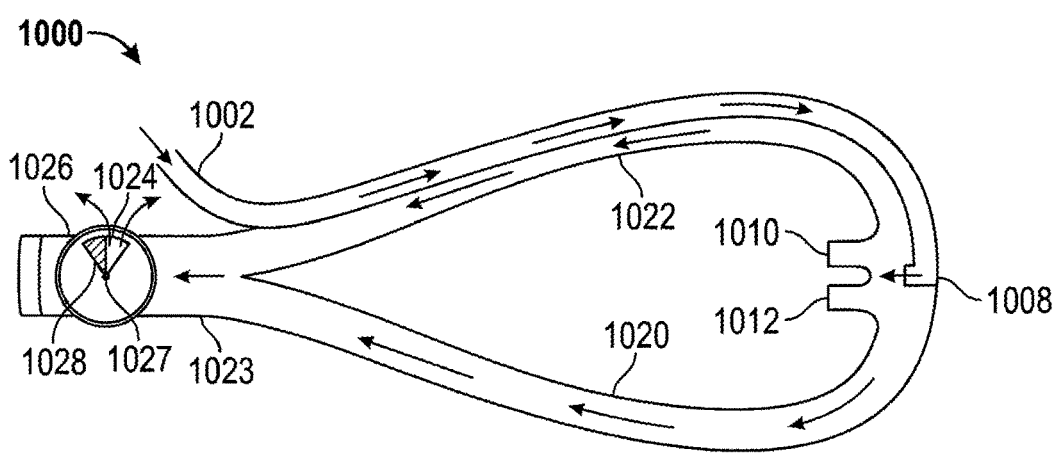
FIG. 18 illustrates a nasal interface device according to another exemplary embodiment of the present invention; with a rotating valve to regulate expiratory gases.

Referring now to FIG. 18, a nasal interface device 1000 according to an alternative exemplary embodiment of the present invention is shown. Nasal interface device 1000 provides a single humidified breathing gas inlet 1002 that is connectable to a source of humidified breathing gas (not shown). Breathing gas inlet 1002 is in fluid communication with a nasal prong assembly 1008. Nasal prong assembly 1008 includes a pair of nasal prongs 1010, 1012 that are insertable into the nares of the patient (not shown) to discharge the humidified breathing gas into the nares.

A pair of expiratory tubes 1020, 1022 are in fluid communication with nasal prong assembly 1008 to allow expiratory gases from the nares to be discharged from nasal interface device 1000. A discharge end of each of expiratory tubes 1010, 1012 is coupled together at discharge portion 1023. Discharge portion 1023 includes an arcuate opening 1024 that allows expiratory gases to exit discharge portion 1023. A rotating wheel 1026 is rotatable about a point 1027. Wheel 1026 has an arcuate opening 1028 that is alignable with arcuate opening 1024 to allow maximum amount of expiratory gases to be discharged from arcuate opening 1024. Alternatively, wheel 1026 may be rotated about point 1027 to reduce the amount of arcuate opening 1024 that is open to atmosphere in order to restrict the amount of expiratory gases that may escape from arcuate opening 1024. Discharge portion 1023 may include a color scale (not shown) similar to color scale 932 discussed above and in conjunction with a chart similar to the exemplary chart discussed above in order to determine approximate back pressures in nasal prong assembly 1008 based on the volume of breathing gas being provided to nasal prong assembly 1008.

Figure 19:
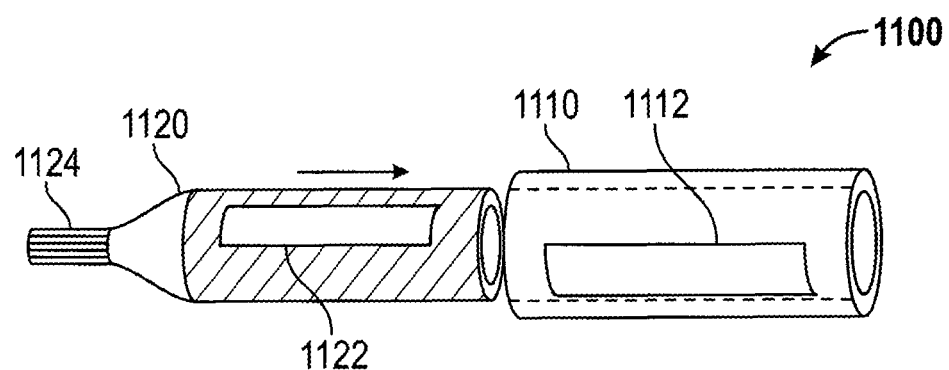
FIG. 19 illustrates an exploded perspective view of an expiratory valve used to regulate discharge of expiratory gas from a nasal cannula.
Figure 19A:
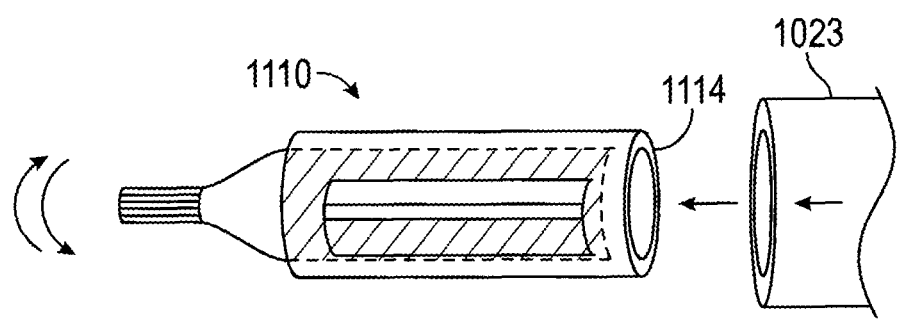
FIG. 19A illustrates the expiratory valve of FIG. 19 being inserted into a discharge portion of a nasal cannula.

An expiratory gas throttling valve 1100 is shown in FIGS. 19 and 19A. Valve 1100 may be used on the expiratory discharge portion of a nasal cannula, such as for example discharge portion 1023 of nasal interface device 1000 without arcuate opening 1024 or rotating wheel 1026. Valve 1100 includes a generally cylindrical outer portion 1110 that includes a generally elongated opening 1112 extending therethrough. A valve insert 1120 includes a generally elongated opening 1122 extending therethrough. Valve insert 1120 also includes a handle 1124. Valve insert 1120 is insertable into outer portion 1110 and is rotatable relative to outer portion 1110 by manipulating handle 1124 so that elongated openings 1112 and 1122 can be aligned with each other to allow maximum discharge of expiratory gases. Alternatively, handle 1124 can be manipulated such that elongated openings 1112 and 1122 are offset from each other, restricting the amount of excretory gases that can be discharged through opening 1112. Discharge portion 1023 may be inserted over an open end 1114 of valve 1100, as shown in FIG. 19A so that expiratory gases from discharge portion 1023 are forced into and through valve 1100.

Although exemplary embodiments of the invention have been disclosed for an illustrative purpose, those skilled in the art would appreciate that many additions, modifications, and substitutions are possible without departing from the scope and spirit of the invention. Further, those skilled in the art will recognize that a particular feature disclosed in one embodiment may be incorporated into another embodiment without express description thereof. For example, PEEP valve 730 disclosed in FIG. 15 may be added to nasal interface device 900 disclosed in FIG. 17 without express disclosure thereof.

What is claimed is:

1. A nasal interface device comprising:
   a breathing gas inlet tube;
   a nasal prong assembly having first and second nasal prongs in fluid communication with the breathing gas inlet tube;
   first and second expiratory tubes extending outwardly from the nasal prong assembly and in fluid communication with the first and second nasal prongs, wherein the first and second expiratory tubes are coupled to each other at an expiratory tube discharge portion, the expiratory tube discharge portion being defined by a side wall and having at least one opening in the side wall; and
   an expiratory gas regulating member operatively disposed over the side wall of the expiratory tube discharge portion and the at least one opening such that the expiratory gas regulating member is operable between a first position in which the at least one opening is at least partially covered by the expiratory gas regulating member and a second position in which the at least one opening is uncovered and open to atmosphere,
   wherein the expiratory gas regulating member comprises a titrating sleeve rotatable relative to the expiratory tube discharge portion at the at least one opening.

2. The nasal interface device according to claim 1, wherein the breathing gas inlet tube comprises a first inlet tube extending along the first expiratory tube and a second inlet tube extending along the second expiratory tube.

3. The nasal interface device according claim 1, wherein the breathing gas inlet tube comprises a single inlet tube extending along the first expiratory tube.

4. The nasal interface device according to claim 3, wherein the single inlet tube includes a discharge portion located between the first nasal prong and a second nasal prong.

5. The nasal interface device according to claim 1, wherein the expiratory tube discharge portion comprises a scale extending along the at least one opening and wherein the titrating sleeve comprises a triangular opening such that, as the titrating sleeve is rotated about the expiratory tube discharge portion, the triangular opening uncovers the scale.

6. The nasal interface device according to claim 5, wherein the scale correlates to back pressure in the expiratory tube discharge portion.

\* \* \* \* \*